United States Patent [19]
Lange, III et al.

[11] Patent Number: 5,429,937
[45] Date of Patent: Jul. 4, 1995

[54] METHOD FOR RECOVERING PURIFIED 100,000 MOLECULAR WEIGHT FRACTION OF HUMAN PANCREATIC CHOLESTEROL ESTERASE USING HEPARIN AGAROSE

[75] Inventors: Louis G. Lange, III; Curtis A. Spilburg, both of St. Louis; Paula M. Kinnunen, University City, all of Mo.

[73] Assignee: CV Therapeutics, Palo Alto, Calif.

[21] Appl. No.: 311,862

[22] Filed: Sep. 26, 1994

Related U.S. Application Data

[60] Division of Ser. No. 936,103, Aug. 26, 1992, Pat. No. 5,352,601, which is a continuation of Ser. No. 655,289, Feb. 14, 1991, abandoned, which is a continuation of Ser. No. 544,212, Jun. 26, 1990, abandoned, which is a continuation of Ser. No. 312,255, Feb. 22, 1989, abandoned, which is a continuation-in-part of Ser. No. 168,424, Mar. 15, 1988, abandoned.

[51] Int. Cl.$^6$ .................. C12N 9/16; A61K 37/54
[52] U.S. Cl. .................... 435/196; 424/94.6; 424/94.61; 435/814; 435/815
[58] Field of Search .................. 435/196, 814, 815; 424/94.6, 94.61

[56] References Cited

U.S. PATENT DOCUMENTS

| | | | |
|---|---|---|---|
| 4,011,138 | 3/1977 | Terada et al. | 435/197 |
| 5,017,565 | 5/1991 | Lange, III et al. | 514/54 |
| 5,063,210 | 11/1991 | Lange, III et al. | 514/54 |
| 5,173,408 | 12/1992 | Lange, III et al. | 435/69.1 |
| 5,352,601 | 10/1994 | Lange, III et al. | 435/196 |

OTHER PUBLICATIONS

Bosuer et al., Proc. Nat'l. Acad. Sci. USA, vol. 85, 7438–42, 1988.
Julien et al; Biochim. Biophys. Acta 280:215–224 (1972).
Vandermeers et al; Biochim. Biophys. Acta 370: 257–268 (1974).
Matsumura et al; J. Biol. Chem. 251 (20): 6267–6273 (1976).
Breuter et al; Biochim. Biophys. Acta 530: 112–123 (1978).
Lombardo et al; Biochim. Biophys. Acta 527: 142–149 (1978).
Tuhackova et al; Biochim. Biophys. Acta 617: 439–445 (1980).
Tsujita et al; Biochim. Biophys. Acta 715: 181–188 (1982).
Durham, III et al; J. Biol. Chem. 259 (12): 7433–7438 (1984).
Treadwell et al., in *Handbook of Physiology*, Section 6, vol. III (1968) pp. 1407–1438.
Brockerhoff et al., in *Lipolytic Enzymes*, Chp. 5 (Academic Press, 1974) pp. 176–193.
Rudd et al., in *Lipases* (Elsevier, N.Y., 1984) pp. 185–204.
Calame et al., (1975) Arch. Bioch. Biophys. 168: 57–65.
Van den Bosch et al., (1973) Biochem. Biophys. Acta. 296: 94–104.
Momsen et al., (1977) Biochem. Biophys. Acta. 486: 103–113.
Guy et al., (1981) Eur. J. Biochem. 117: 457–460.
Casdorph H. R., in *Lipid Pharmocology* (Academic Press, 1976) pp. 221–256.
Ayotte and Perlin, (1986) Carbohydrate Res. 145: 267–277.
Cardin et al., (1984) Thrombosis Res. 34: 541–550.

*Primary Examiner*—David M. Naff
*Assistant Examiner*—Michael V. Meller
*Attorney, Agent, or Firm*—Allegretti & Witcoff, Ltd.

[57] ABSTRACT

Intestinal cell endogenous heparin mediated absorption of cholesterol or fatty acids in mammals is inhibited through the oral administration of heparin, an active heparin subfraction or heparinase. Suppression of cholesterol esterase-mediated absorption in humans can be inhibited by soluble heparin by two mechanisms, i.e. displacement of the enzyme from the intestinal cell membrane and inhibition of enzymatic activity of the displaced enzyme.

1 Claim, 6 Drawing Sheets

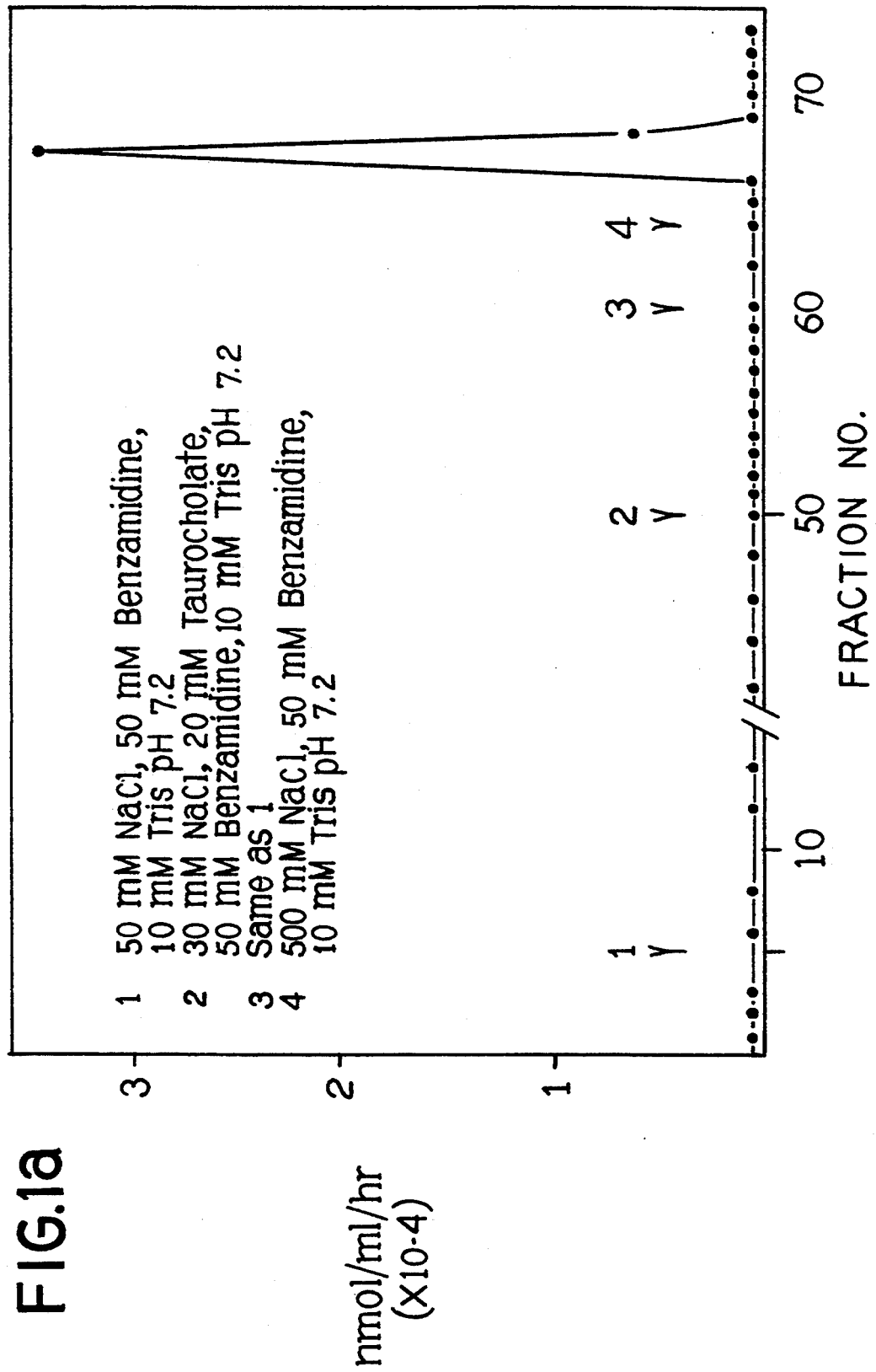

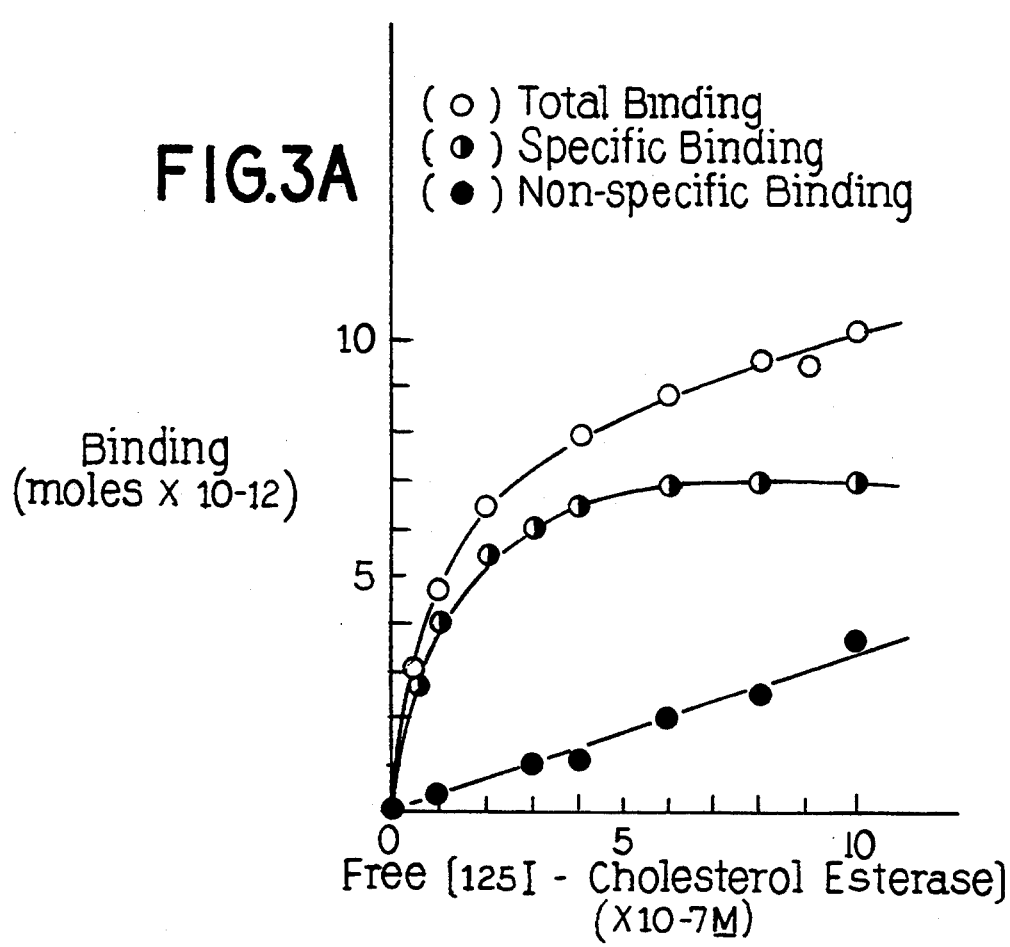
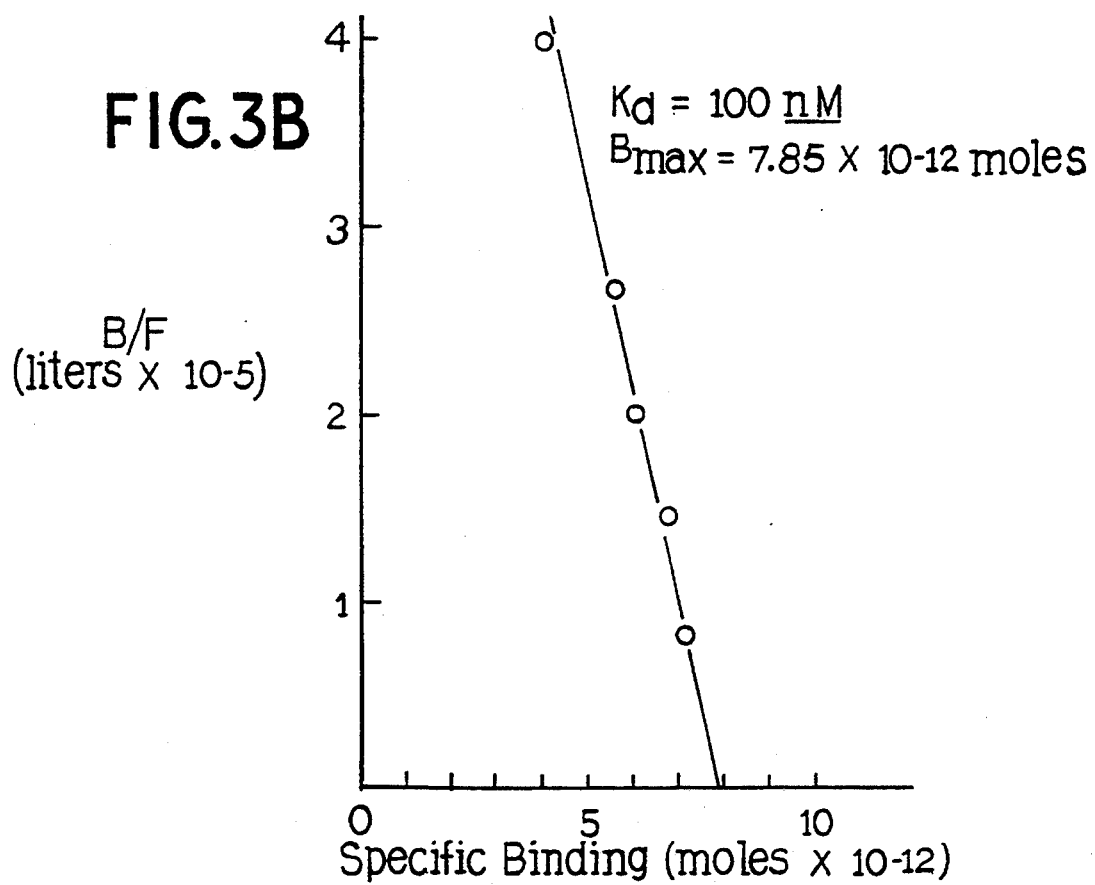

METHOD FOR RECOVERING PURIFIED 100,000 MOLECULAR WEIGHT FRACTION OF HUMAN PANCREATIC CHOLESTEROL ESTERASE USING HEPARIN AGAROSE

This application is a divisional of Ser. No. 936,103 filed Aug. 26, 1992, now U.S. Pat. No. 5,352,601, which is a continuation of Ser. No. 655,289, Feb. 14, 1991, abn., which is a continuation of Ser. No. 544,212, Jun. 26, 1990, abn., which is a continuation of Ser. No. 312,255, Feb. 22, 1989, abn., which is a continuation-in-part of Ser. No. 168,424, Mar. 15, 1988, abn.

BACKGROUND OF THE INVENTION

This invention relates to the inhibition of intestinal cholesterol absorption in mammals and, more particularly, to inhibiting or decreasing intestinal cholesterol absorption by the oral administration of heparin or heparin subfractions. The invention is based upon our discovery of a novel molecular pathway for the absorption of ingested cholesterol/cholesteryl esters and the identification of specific sites in this pathway for drug intervention to decrease intestinal cholesterol absorption.

Atherosclerosis is the leading killer in the United States, and yet detailed understanding of the absorption of cholesterol, an essential factor in the development of atherosclerosis, has remained rather sketchy, despite the fact that restrictions of dietary intake of cholesterol are the mainstay of therapeutic regimens according to current medical practice. It is known that the principal dietary form of cholesterol is a series of related fatty acid esters of cholesterol and that these must be hydrolyzed before intestinal absorption of cholesterol occurs (Treadwell et al., Handbook of Physiology, Alimentary Canal, Section 6, Vol. III, 1968). Pancreatic cholesterol esterase is known to catalyze the hydrolysis of cholesteryl esters but knowledge has remained rudimentary concerning these enzymes due to a lack of a general method for their preparation in homogeneous form, to the frequent use of artificial, colorimetric substrates in lieu of cholesteryl ester in their assay and to the failure to minimize or eliminate artifacts due to the presence of pancreatic proteases in their preparation (Brockerhoff et al., (1974) In: Lipolytic Enzymes, Chapter V, pp. 177-192, Academic Press, New York and Rudd et al., (1984) In: Lipases, pp. 185-204, Elsevier, N.Y.). Accordingly, no unified conceptualization of the role of cholesterol esterase, buttressed by experimental documentation, has emerged. Thus, rat pancreatic cholesterol esterase, the most commonly studied one, is reported as a 67,000 (67K) species that hexamerizes in the presence of taurocholate to form an active enzyme (Calame et al., (1975) Arch. Biochem. Biophys. 168: 57-65). Bovine cholesterol esterase is also 67K, but the porcine and human enzymes are reported as 83K and 100K, respectively (Van den Bosch et al., (1973) Biochem. Biophys. Acta 296: 94-104; Momsen et al. (1977) Biochem. Biophys. Acta 486: 103-113; and Guy et al. (1981) Eur. J. Biochem. 117: 457-460). These differences have not been satisfactorily explained nor the role of taurocholate rigorously examined, but some of these dissimilarities may reflect use of colorimetric substrates for assay instead of cholesterol esters.

Because of these deficiencies, no generally accepted hypothesis has been advanced to explain in molecular details the nature of cholesterol absorption in the intestine, no selective inhibitors have been reported, and the mechanism of re-esterification of cholesterol in the intestinal cell before transport to the liver has not been elucidated.

Despite these shortcomings in prior investigations, one of the primary forms of therapy for patients with elevated cholesterol in the blood has been modulation of intestinal cholesterol absorption, either by serious counseling to eat less cholesterol or through the use of bile salt (derived from cholesterol) binding resins such as cholestyramine which are poorly tolerated (Casdorph, H. R. (1976) In: Lipid Pharmacology, pp. 222-256, Academic Press, New York).

Also, because fatty acids, especially saturated ones, play an essential role in atherogenesis, inhibition of their intestinal absorption should diminish rates of atherogenesis.

There has been a continuing need, therefore, for more fundamental knowledge of the mechanism of cholesterol absorption and improved and effective means for inhibiting intestinal cholesterol and fatty acid absorption in mammals.

SUMMARY OF THE INVENTION

Among the several objects of the present invention may be noted the provision of an effective method for inhibiting intestinal cell endogenous heparin mediated absorption of cholesterol or fatty acids in mammals; the provision of such a method which is conveniently effected through the oral administration of heparin, heparinase or an active heparin subfraction; and the provision of a method for inhibiting intestinal cholesterol or fatty acid absorption which minimizes or reduces toxic side effects. Other objects and features of the invention will be in part apparent and in part pointed out hereinafter.

In brief, the present invention is directed to a method for inhibiting intestinal cell endogenous heparin mediated absorption of cholesterol or fatty acids in mammals by orally administering to a mammal an effective amount of heparin, heparinase or an active heparin subfraction.

DESCRIPTION OF THE DRAWINGS

FIG. 1a is a graph showing the results of heparin chromatography of human cholesterol esterase;

FIG. 3 is constituted by two graphs showing the binding of $^{125}$I-labeled cholesterol esterase to intestinal vesicles;

DESCRIPTION OF THE PREFERRED EMBODIMENTS

Figure 1B:
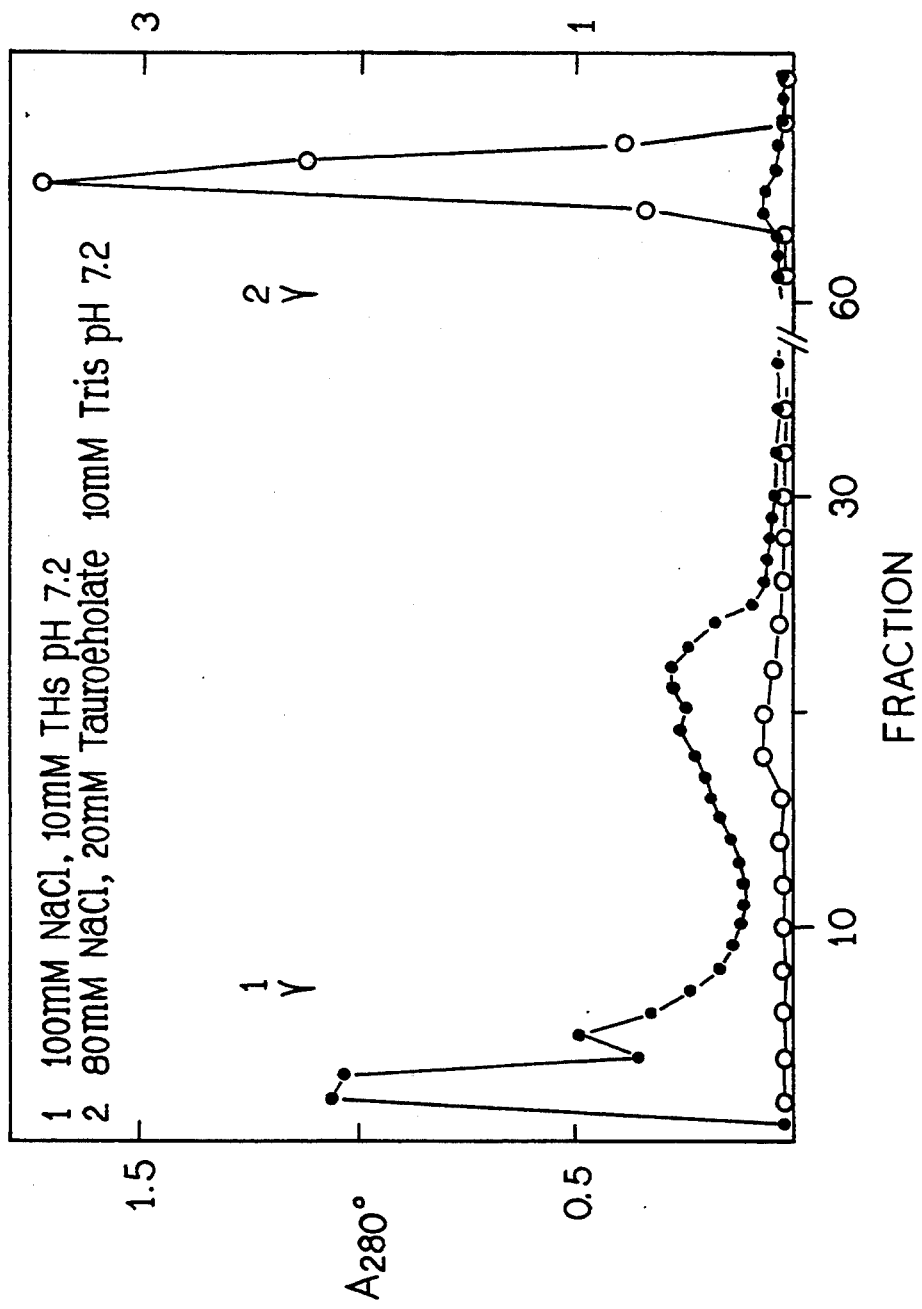
FIG. 1b is a graph showing the results of heparin chromatography of bovine cholesterol esterase.

In accordance with the present invention, we have made certain discoveries concerning the nature of cholesterol absorption in the intestine, including discoveries as to the nature of pancreatic cholesteral esterases, the mechanism for the absorption of cholesterol and, most importantly, we have discovered inhibitors for effectively decreasing or reducing intestinal cholesterol or fatty acid absorption in mammals.

Our investigations indicate that the nature of cholesterol absorption in the intestine is extremely complex on a molecular basis and we have identified a number of novel steps in its absorption. Thus, human pancreatic cholesterol esterase, the enzyme responsible for hydrolyzing the principal dietary form of cholesterol, i.e., cholesterol esters, was previously thought to exist in only one molecular form, but has now been found by us to consist of four molecular weight forms with approximate molecular weights of 210,000, 100,000, 67,000; and 52,000. For the proper absorption of cholesterol, the large molecular weight forms of this enzyme are secreted by the pancreas and arrive in the intestine where cholesterol esters are hydrolyzed. Moreover, our studies demonstrate that these high molecular weight forms of the enzyme bind reversibly to heparin, a natural component of the membrane of the intestinal cell. Importantly, this binding allows the enzyme to be localized in the proximity of the membrane, across which cholesterol is absorbed, and to permit hydrolysis of cholesterol esters at the intestinal cell membrane. Once cholesterol is hydrolyzed and absorbed, it needs to be reesterified in the intestinal cell. Two subsequent molecular weight forms of cholesterol esterase were thus identified by us, including the 67,000 and 52,000 molecular weight forms. These forms would appear to be responsible for transport of cholesterol for the resynthesis of cholesterol esters in the intestinal cell before absorption into the blood and lymph.

Based upon these observations and findings, we discovered that orally administered heparin, heparinase and active heparin subfractions could compete for binding to cholesterol esterase, thereby displacing the enzyme from the membrane of the intestinal cell and greatly diminishing the intestinal absorption of cholesterol and cholesterol-derived fatty acids normally resulting from deesterification or hydrolysis of cholesterol esters. As used herein, the term "heparin" includes heparin and heparin-containing materials such as heparin polymers. We have also discovered that pancreatic enzymes such as triglyceride lipase which hydrolyze triglycerides into free fatty acids are displaced from the membrane of the intestinal cell by exogenous heparin thereby diminishing intestinal absorption of fatty acids. The experimental results set forth hereinafter indicate that in cholesterol-fed rabbits the administration of heparin by mouth leads to a 70% decrease in the amount of cholesterol absorbed, compared to cholesterol-fed animals that received saline instead of heparin. Accordingly, a dramatic reduction in cholesterol absorption is achieved by administration of oral heparin. Because heparin is absorbed very poorly from the GI tract and thus is not effective in producing anti-coagulation, it has not been used orally for any standard medical condition. However, for the purposes of inhibiting intestinal cholesterol absorption in accordance with the present invention, this poor absorption of heparin after oral administration is a great advantage since it confers selectivity to the method of the invention and potentially markedly reduces side effects that could be produced by compounds that are successfully absorbed from the GI tract.

The following summarizes our discoveries concerning cholesterol esterase isolation, heparin interaction with cholesterol esterase, isolation of an active subfraction of heparin and the in vivo studies which we have carried out to establish the effectiveness of orally administered heparin in inhibiting intestinal cholesterol absorption in mammals.

a) Cholesterol Esterase Isolation

First, we devised a general method for the isolation and purification of pancreatic cholesterol esterase that results in homogeneous enzyme from human, bovine, porcine or rat pancreas. This general method relies upon our discovery that cholesterol esterases bind to heparin-Sepharose. This procedure involves the preparation of a pancreatic extract in the presence of 50 mM benzamidine, a protease inhibitor, followed by hydroxylapatite chromatography, AcA 34 gel permeation chromatography, and finally chromatography over heparin immobilized to Sepharose. Assay is carried out by quantitating the release of $^{14}$C-oleate from cholesteryl $^{14}$C-oleate (a cholesteryl ester) embedded in a liposome.

For human pancreas, four forms of cholesterol esterase have been detected, all of which react positively in a western blot to anti-cholesterol esterase antibody. These forms have molecular weights of, approximately, 210K, 100K, 67K and 52K; only the 100K has been previously described. Proportionately they are present in amounts of 5%, 45%, 5% and 45%, respectively. Elution of the species from heparin-Sepharose indicates that the 210K, 100K and 52K species bind very tightly and require 0.5M NaCl for elution, while 5 to 20 mM taurocholate (the intestinal concentration of this bile salt) is ineffective. On the other hand, the 67K form can be eluted with 5 to 20 mM taurocholate (or 0.5M NaCl). All four species are homogeneous as judged by SDS-PAGE. While all species appear to catalyze the hydrolysis of cholesteryl esters, the ratio of hydrolysis/synthesis decreases markedly with decreasing molecular weight, such that the 52K form is principally a cholesterol ester synthesizing enzyme and represents, therefore, a novel pathway for the synthesis of cholesterol esters.

Application of this procedure to porcine, bovine or rat pancreas produces homogeneous cholesterol esterase in patterns similar to that seen in human pancreas: porcine (180, 83, 52K); bovine (180, 72, 52K); rat (180, 67, 52K). These species are also all cross-reactive in Western blots with anti-cholesterol esterase antibody. Such results indicate that cholesterol esterase consists of a family of related proteins that share a common epitope, having a range of cholesterol ester hydrolytic/synthetic capabilities and heparin-binding affinities.

b) Heparin Interaction with Cholesterol Esterase

Cholesterol has a very low critical micelle concentration. Thus, if produced by cholesterol esterase catalyzed hydrolysis of cholesterol esters in the bulk fluid phase of intestinal juice far from the intestinal cell membrane across which it is absorbed, free cholesterol would likely be simply excreted. We therefore considered the likelihood that intestinal cell membrane heparin functions as a receptor for cholesterol esterase. Indeed, small intestine is one of the chief sources of commercially available heparin, but no in vivo function has been ascribed to it. Such an interaction would facilitate the production of sub-critical micelle concentrations of cholesterol at the absorptive membrane.

Our studies indicate that binding of human pancreatic cholesterol esterase to heparin immobilized on Sepharose is highly specific: 2.5 mg/ml heparin elutes 5 greater than 90% of bound enzyme, while 5 mg/ml chondroitin sulfate is completely ineffective in elution. Cholesterol esterase also binds to vesicles of small intestine which display endogenous heparin on their surface. These are prepared by vortexing a homogenate of rabbit small intestine in 10 mM Tris-Cl, pH 7.4 followed by preparative centrifugation at 50,000× g for 60 minutes and vesicles contain 50 ug heparin/mg protein, approximately 50% of which is surface available. Human pancreatic cholesterol esterase (100K form) binds to these vesicles with saturation kinetics. Scatchard analysis indicates a $K_D$ of 100 nM. Displacement with 150 mM NaCl or 10 mg/ml chondroitin sulfate is ineffective, but displacement with heparin is concentration-dependent over the range 0.5 to 10 mg/ml. Pretreatment of the vesicles with bacterial heparinase also prevents cholesterol esterase binding. All these results indicate that cholesterol esterase can bind to its receptor (intestinal cell heparin) to localize it near the absorptive membrane where it can cleave ingested cholesteryl esters to free cholesterol for absorption. Accordingly, oral heparin administration should reduce absorption of cholesterol after its ingestion.

Studies employing intestinal cells as well as soluble heparin have demonstrated several very important features of the interaction of heparin with cholesterol esterase as well as elucidated marked species differences in this interaction. For example, binding of human pancreatic cholesterol esterase to intestinal cell membrane is essential for cellular uptake of cholesterol derived from cholesterol esters. In the absence of enzyme or taurocholate, which serves to activate the enzyme, no cholesterol is absorbed. Importantly, when cholesterol esterase is present together with taurocholate, there is a rapid uptake of cholesterol, which can be virtually completely suppressed by the addition of exogenous heparin. In this case, exogenous heparin not only displaces bound enzyme from the membrane, but for the human pancreatice 100K species heparin is a very potent inhibitor of cholesterol esterase, with a $K_i$ of approximately 200 nM for bulk heparin. In contrast, membrane-bound heparin, such as that found in the intestinal cell membrane, is a poor inhibitor. Moreover, human pancreatic cholesterol esterase is much more sensitive to inhibition by exogenous soluble heparin than is bovine cholesterol esterase ($K_i$=300 uM for the 67K form and infinity for the 72K species). Thus, supression of cholesterol esterase-mediated absorption in humans can be inhibited by soluble heparin by two mechanisms—displacement of the enzyme from the membrane and inhibition of enzymatic activity of the displaced enzyme.

Further, fatty acids are produced after cleavage of cholesterol esters and therefore disruption of the interaction between cholesterol esterase and the membrane-bound heparin should diminish fatty acid absorption as well as cholesterol absorption.

Figure 4:
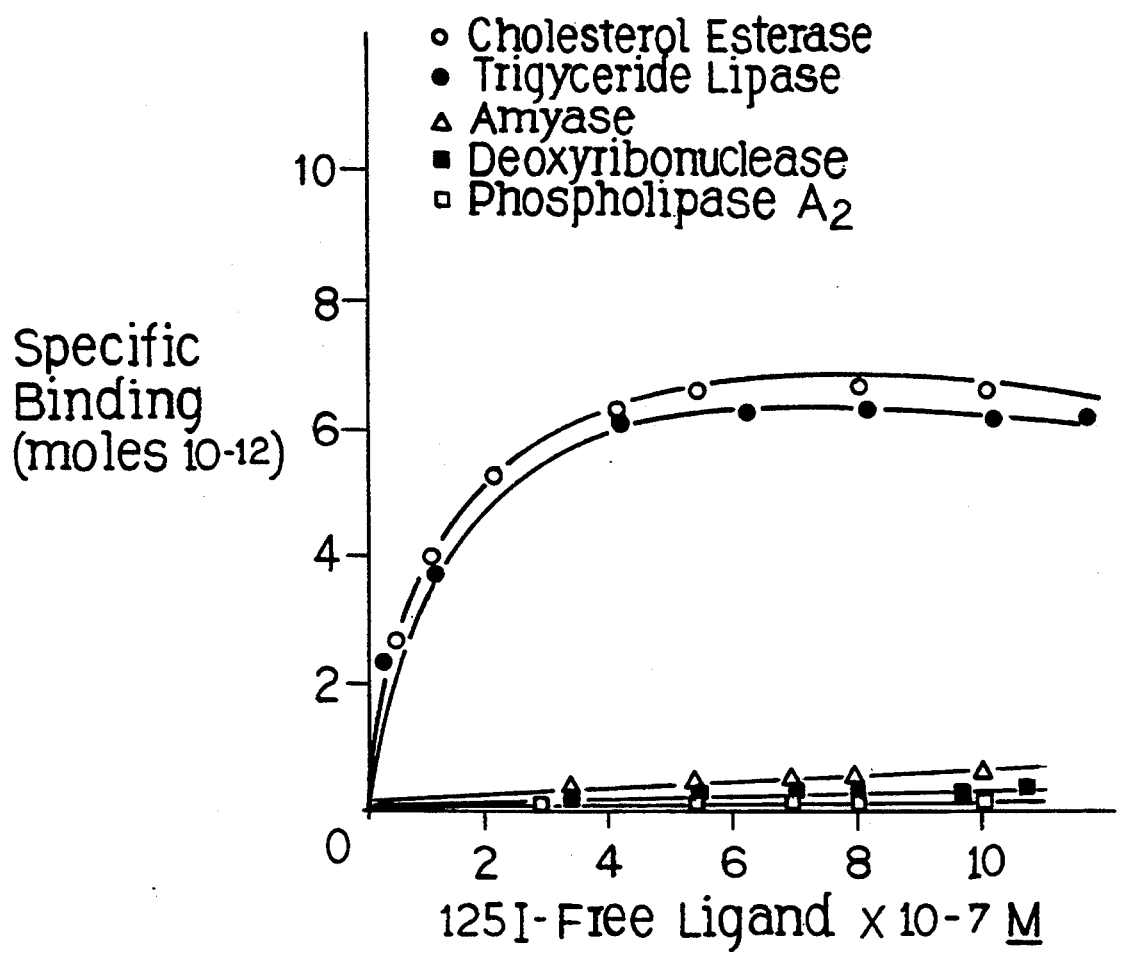
FIG. 4 is a graph showing the binding of neutral lipolytic pancreatic enzymes to small intestine membrane vesicles.

Further, as described in FIG. 4, triglyceride lipase binds in a similar manner to small intestine vesicles. Because its cleavage of triglycerides provides the majority of fatty acids for absorption, at least two pathways for fatty acid uptake can be prevented by exogenous heparin.

c) Isolation of an Active Sub-fraction of Heparin

Because heparin is a heterogeneous mixture of sulfated polysaccharides, this crude material was fractionated using low density lipoprotein conjugated to Sepharose (Cardin et al., (1984) Thrombosis Res. 34: 541–550). Approximately 5% of bulk heparin bound tightly to this conjugate and was eluted with 0.5 M NaCl. Binding studies using this tight-binding fraction of heparin and the small intestine vesicle assay described above indicated that this fraction is approximately 100-fold more effective than bulk heparin in displacing cholesterol esterase from these vesicles. In addition, the inhibition of the 100K human pancreatic cholesterol esterase is inordinately strong, with a $K_i$ of 2 nM (20 ng/ml). Thus, a definable sub-fraction of bulk heparin is responsible for cholesterol esterase binding and can effectively block enzyme binding and enzymatic activity in the human.

d) In Vivo Studies

Investigations in the cholesterol-fed rabbit indicate that orally administered heparin is effective in reducing intestinal cholesterol absorption. Thus, rabbits (n=4 in each group) were fed 2% cholesterol for 14 days. After this time, oral heparin (2 mg/ml) was administered to the experimental group in drinking water for 48 hours before the experiment, while the control group received only drinking water. The experiment was initiated by the administration of $^3$-cholesteryl-oleate by mouth to all rabbits, followed orally by either 10 ml water or heparin, 2 mg/ml, respectively. After four hours, blood was sampled and the livers removed. The amount of $^3$H-cholesterol and their esters were quantitated in each after lipid extraction and thin-layer chromatography. The heparin-treated group had 30% less $^3$H-cholesterol in the blood and 50% less in liver. These studies demonstate that oral heparin is effective in diminishing intestinal cholesterol absorption in vivo.

The inhibiting agents of the invention may be orally administered in the form of compositions comprising the agent and a pharmaceutical carrier which may be either liquid or solid material. The compositions may be administered in the usual pharmaceutical forms including capsules, tablets, solutions, suspensions and the like. For example, the inhibiting agents may be formulated with carriers such as magnesium stearate and lactose and filled into gelatin capsules. Other solid pharmaceutical carriers known to the art such as fillers, binders and lubricants may also be employed. The daily dosage may vary widely from, for example, 5 to 10 mg/day for an active heparin subfraction to 100 mg to 1 g/day for bulk heparin.

The following examples illustrate the practice of the invention.

EXAMPLE 1

In a typical preparation, 30 gm of human pancreas received at autopsy were placed in 10 mM phosphate, pH 6.0, 50 mM benzamidine, 0.5% digitonin, and homogenized with a polytron. The mixture was centrifuged at 48,000× g for 30 minutes, the supernatant collected and then recentrifuged for one hour at 100,000× g. The cytosol-containing supernatant was passed through glass wool to remove fat, and the clear solution was used as starting material for enzyme purification.

Pancreatic cytosol was dialyzed overnight against 10 mM phosphate, pH 6.8, 50 mM benzamidine and applied at 30 ml/hr. to hydroxylapatite (2.6×10 cm) equilibrated with the same buffer. The resin was washed with one column volume of equilibration buffer, one column volume of 50 mM phosphate, pH 6.8, 50 mM benzamidine and then developed with a linear gradient from 50 mM phosphate, pH 6.8, 50 mM benzamidine to 350 mM phosphate, pH 6.8, 50 mM benzamidine. Cholesterol esterase(s) was eluted as a single peak, pooled and concentrated ten-fold with an Amicon ultrafiltration cell, equipped with a YM-10 membrane. The concentrated protein was applied at 17 ml/hr. to Ultragel AcA 34 (2.6×90 cm) equilibrated with 0.50M NaCl, 10 mM phosphate, pH 6.0 and the enzyme emerged as a single peak. Cholesterol esterase from the AcA 34 column was pooled, dialyzed against 10 mM phosphate, pH 6.0, and the sample was then chromatographed on heparin agarose, equilibrated with the same buffer (see FIG. 1a). All the activity was bound to the resin which was then washed with 50 mM NaCl, 50 mM benzamidine, 10 mM Tris pH 7.2 to remove protein impurities. The resin was then washed with 30 mM NaCl, 20 mM taurocholate, 50 mM bezamindine, 10 mM Tris pH 7.2, which removed a small amount of activity (<1%). The bile salt was washed from the column with 50 mM NaCl, 50 mM benzamidine, 10 mM Tris pH 7.2 and the resin was then washed with 500 mM NaCl, 50 mM benzamidine, 10 mM Tris pH 7.2. For buffer wash 1 indicated in FIG. 1a, 30 minute fractions were collected, while for buffer washes 2–4, 12 minute fractions were collected. The resulting high salt eluted 90% of the applied cholesterol esterase activity and produced two bands on SDS-PAGE; the major band had molecular weight 100,000 while the minor band had molecular weight 210,000. Both bands reacted positively in a Western blot to bovine anti-cholesterol esterase antibody. The overall yield of purification was approximately 40% with a 150-fold purification.

EXAMPLE 2

The following method allows isolation of a 67K species of human pancreatic cholesterol esterase. Human pancreatic cytosol was dialyzed against 5 mM benzamidine, 1 mM 2-mercaptoethanol, 3.5 mM Tris pH 8.0 and then applied to DEAE cellulose (2.5×15 cm), equilibrated with the same buffer. The resin was washed at 30 ml/hr with several column volumes of buffer and then developed with a linear gradient running from 5 mM benzamidine, 1 mM mercaptoethanol, 3.5 mM Tris pH 8.0 to 250 mM NaCl, 5 mM benzamidine, 1 mM mercaptoethanol, 3.5 mM Tris pH 8.0. Cholesterol esterase activity was eluted at approximately 0.10M NaCl, pooled, concentrated to 5 ml and applied to a gel filtration column. The column was developed as described in Example 1. Activity was pooled and dialyzed against 10 mM phosphate pH 6.0. The pH of the sample was raised to 7.2 by adding 1M Tris and it was then applied to heparin agarose equilibrated with 10 mM Tris pH 7.2. The column was washed with 100 mM NaCl, 10 mM Tris pH 7.2 and finally, with 500 mM NaCl, 10 mM Tris pH 7.2 to remove active enzyme. Examination on SDS-PAGE showed several bands centered at 67,000.

EXAMPLE 3

Human pancreatic cholesterol esterase (52K form) can be isolated as follows. Cytosol prepared as above from 30 g pancreas is dialyzed versus 10 mM Tris-Cl, 50 mM benzamidine, pH 8.2 and then chromatographed over DEAE cellulose (2.6×25 cm). Unlike the higher molecular weight forms of cholesterol esterase which bind under these conditions, the 52K species rapidly passes through DEAE cellulose at pH 8.2, with a 40-fold purification and 80% yield. Subsequent chromatography over hydroxylapatite and heparin-Sepharose yields a homogeneous protein (SDS-PAGE, M.W.=52K) with enzymatic activity expressed principally in the synthetic direction for cholesterol esters (rate of synthesis/rate of hydrolysis=10/1). This species also cross-reacts in Western blotting to anti-cholesterol esterase antibodies.

EXAMPLE 4

Figure 2:
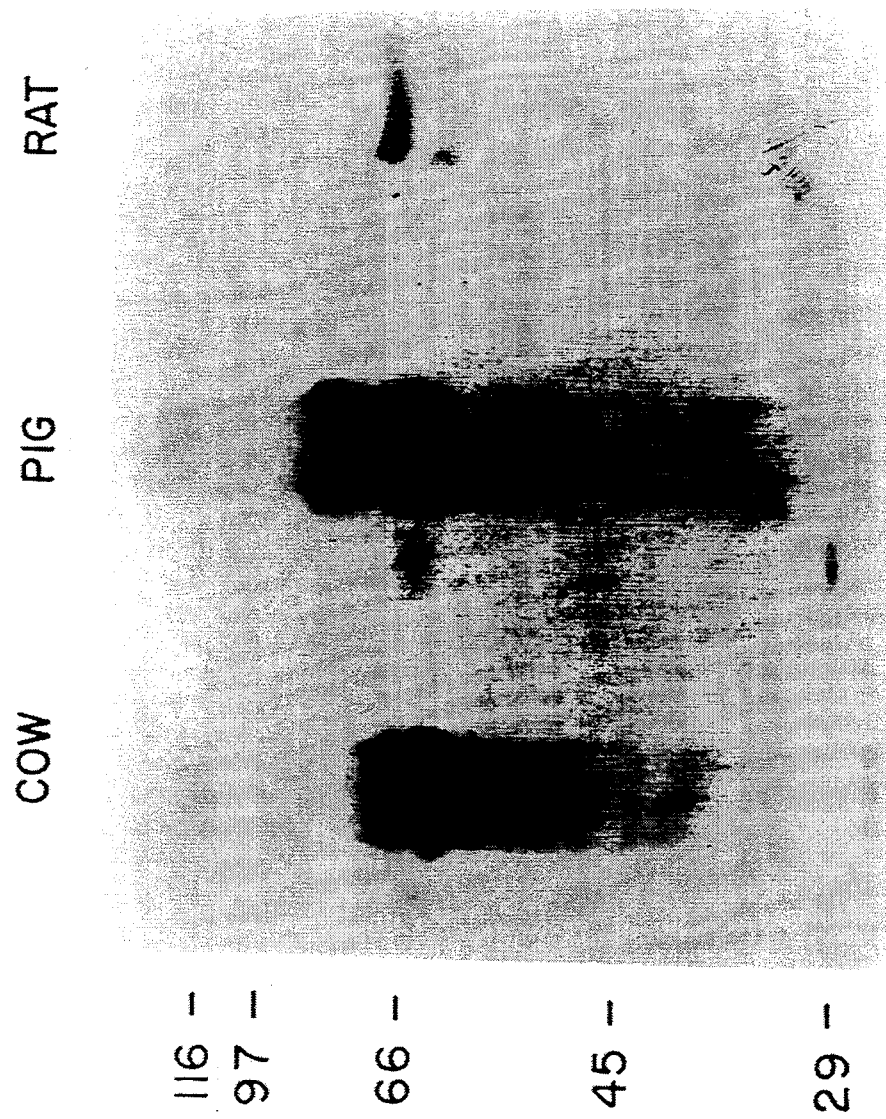
FIG. 2 is an immunoblot of cholesterol esterase from cow, pig and rat pancreas.

The procedures described above have been extended to other species with the following results (See FIG. 1b and FIG. 2).

For the results shown in FIG. 1b, thirty milligrams of commercially available enzyme were dissolved in 10 mM Tris, pH 7.2 and pumped at 15 ml/hr onto a heparin-Sepharose column equilibrated with the same buffer. The column was then washed with buffers 1 and 2 as indicated in FIG. 1b. For buffer 1, 30 minute fractions were collected; for buffer 2, 10 minute fractions were collected.

FIG. 2 is an immunoblot of cholesterol esterase from cow, pig and rat pancreas. Fresh tissue was homogenized in 50 mM benzamidine, 10 mM phosphate, pH 6.8, plus digitonin and then dialyzed against 50 mM benzamidine, 10 mM phosphate, pH 6.8, followed by dialysis against 10 mM phosphate, pH 6.0. The sample was then pumped onto a heparin-Sepharose column and washed with several column volumes of 50 mM NaCl, 50 mM benzamidine, 10 mM Tris, pH 7.2. All the cholesterol esterase activity was removed with 500 mM NaCl, 50 mM benzamidine, 10 mM Tris, pH 7.2, and then lyophilized. Samples were then run on SDS-PAGE using 7.5% acrylamide as the separating gel and 4.5% acrylamide as the stacking gel. Immediately following electrophoresis, the protein was transferred to nitrocellulose and then incubated with rabbit anti-bovine cholesterol esterase antibody. After washing, the nitrocellulose sheet was incubated with $^{125}$I-Protein A, dried and exposed to x-ray film.

Using fresh pig pancreas, cholesterol esterase forms are found at 180K, 83K and 52K. The purification summary for pig cholesterol esterase (83K) is set forth in the following table:

| Step | Protein ($A_{280}$) | Total Act.[a] $\times 10^{-3}$ | Sp. Ast. $\times 10^{-3}$ | Recovery (%) | Purification (x-fold) |
| --- | --- | --- | --- | --- | --- |
| Cytosol | 2,034 | 5,715 | 2.8 | 100 | 1.0 |
| Hydroxylapatite | 498 | 3,445 | 6.9 | 60 | 2.5 |
| AcA 34 | 58 | 2,110 | 36.2 | 37 | 12.9 |
| Heparin | 9.8 | 1,309 | 134.2 | 23 | 50.0 | a = nmoles/hr

Using rat pancreas, cholesterol esterase forms are found at 180K, 67K and 52K. Using bovine pancreas, cholesterol esterase forms are found at 180K, 72K and 52K. Human pancreatic cholesterol esterase forms are 210K, 100K, 67K and 52K.

EXAMPLE 5a

Exogenous heparin inhibits the interaction and binding of pancreatic choleserol esterase to small intestine vesicles prepared from proximal small intestine segments homogenized in 10 mM Tris-Cl, pH 7.2, and centrifuged at 48,000× g for 45 minutes. Vesicles contained 1.0 mg protein/ml, 30 ug total cholesterol/mg protein and 50 ug endogenous heparin/mg protein. $^{125}$I-cholesterol esterase (100K or 67K form) was added (0 to 400 pmol; 2,000 dpm/pmol) to 100 ug of protein of small intestine vesicles in 10 mM Tris-Cl, pH 7.2 for 15 min. at 37°. The concentration of offered $^{125}$I-cholesterol esterase varied between 10 nM and 1 uM. Experiments were performed utilizing 1% blotto to decrease nonspecific protein binding to the vesicles. After the 15 minute incubation at 37°, the reaction was quenched and the assay mixtures were filtered through wells of a Millipore system containing 0.2 micron pore filters presoaked in buffer. The filtrate was collected to assess free (unbound) enzyme, and the filters were then immediately washed with 15 ml of cold buffer and counted for $^{125}$I. Total binding was defined as $^{125}$I-dpm bound to filter paper minus $^{125}$I-dpm detected in the same reaction without vesicles (background). Nonspecific binding (radioactivity bound to the vesicles in the presence of excess cold ligand) was quantitated as the amount of $^{125}$I-cholesterol esterase binding in the presence of a 1000-fold molar excess of unlabeled cholesterol esterase as described above. Specific binding is defined as the difference between total bound dpm and nonspecific-bound dpm (converted to moles bound by dividing by the SRA).

Graphical analysis indicated saturation binding. Binding in the presence of a 1000-fold molar excess of cold cholesterol esterase established a nonspecific binding curve. A difference curve between the two represents specific binding of $^{125}$I-cholesterol esterase to small intestine vesicles with a $K_D$ of 100 nM (FIG. 3). When included in the binding assay, exogenous heparin decreases binding of $^{125}$I-cholesterol esterase to vesicles in a concentration-dependent manner with increasing concentrations of heparin from a 0.5 to 100-fold molar excess compared to surface-bound vesicular heparin: specific binding in the presence of heparin decreased by 5% to 72% in the presence of 0.5 to 100-fold molar excesses of heparin, respectively. Specificity of binding was demonstrated since chondroitin sulfate at 0.5 to 100-fold molar excesses decreased specific binding less than 10%, isotonic saline had no effect and pretreatment of vesicles with bacterial heparinase diminished specific binding by 75%. Lastly, binding of the 100K and 67K form of cholesterol esterase in the presence of 5 mM taurocholate showed that the 100K form retained 72% specific binding while the 67 form retained only 20%. These results indicate that pancreatic cholesterol esterase binds to small intestine through a receptor-like interaction with endogenous heparin and that exogenous heparin can significantly reduce this interaction.

EXAMPLE 5b

Cellular uptake of $^3$H-cholesterol from $^3$H-cholesterol oleate is dependent on the presence of cholesterol esterase and is markedly inhibited by the addition of soluble heparin. For example, intestinal cells (colonic adenocarcinoma cells CaCo-2, American Type Cell Culture) were grown in T150 flasks in medium consisting of DME, 10% v/v fetal bovine serum, 50 ug/ml gentamicin and 2 mM sodium pyruvate. Uptake experiments were conducted using $10^5$ intestinal cells in PBS buffer containing 5 mM CaCl$_2$, pH 7.4 in the presence of 5 uM $^3$H-cholesterol oleate (SRA=50 dpm/pmol) embedded in phosphatidylcholine vesicles along with 10% v/v lipoprotein-depleted serum and 1.5 mM taurocholate. At time zero, 5 nM human pancreatic cholesterol esterase (100K, homogeneous) was added to one set of flasks, an equivalent volume of buffer to another set, and 1 mg/ml final concentration bulk heparin together with 5 nM enzyme to a third set. At selected times, i.e., 0, 15, 30, 60, 120 and 480 min, medium was removed and the cells were washed with medium to allow quantitation of $^3$H-cholesterol uptake. In the absence of enzyme, cellular uptake of $^3$H-cholesterol was linear and occurred at a rate of 40 dpm/hr/$10^5$ cells. In the presence of cholesterol esterase, the rate of $_3$H-cholesterol uptake was 1,800 dpm/hr/$10^5$ cells. Importantly, in the presence of heparin, uptake was significantly suppressed and occurred at a rate of 500 dpm/hr/$10^5$ cells. Thus, exogenous soluble bulk heparin can significantly inhibit the uptake of cholesterol into intestinal cells commonly used to study transport phenomena.

EXAMPLE 6

Subfractionation of heparin produces a high reactive form that is 100-fold more effective in displacing bound cholesterol esterase from small intestine vesicles. First, low density lipoprotein (LDL) was isolated by density gradient centrifugation from a rabbit which had been fed cholesterol for three weeks. After immobilization of LDL to Sepharose, bulk commercial heparin (from pig intestine) was applied to the LDL conjugate in 10 mM Tris-Cl, pH 7.2, the resin washed with five column volumes of buffer and a fraction eluted by addition of 0.5M NaCl. Approximately 5% of applied heparin was recovered in the NaCl wash. After removal of salt, this high reactive form of heparin was evaluated in the vesicle assay. On a weight basis, this subfraction was 100-fold more potent in displacing bound $^{125}$I-cholesterol esterase when compared to bulk heparin. The unreactive heparin that passed through the LDL Sepharose resin was completely ineffective.

Importantly, this high reactive heparin is also a very potent inhibitor of human pancreatic cholesterol esterase (100K). Whereas bulk heparin has a $K_i$ of 200 nM for this enzyme, unreactive heparin is non-inhibitory and high-reactive heparin has a $K_i$ of 2 nM.

EXAMPLE 7

Male New Zealand white rabbits (1±0.1 kg) were fed (n=4 in each group) 2% cholesterol Purina Rabbit Chow for two weeks plus either tap water or oral heparin (2 mg/ml) for 48 hours prior to the experiment. On day 15, the heparin pretreated rabbits received 100 mg heparin in 10 ml water followed by 10 ml of radiolabeled liquid rabbit Chow containing 50 uCi of [1,2,6,7-$^3$H] cholesteryl oleate and the control group received 10 ml H$_2$O followed by 10 ml of the same radiolabeled Chow. After four hours without food and water, the rabbits were sacrificed and the amount of $^3$H-cholesterol and $^3$H-cholesteryl esters quantitated in liver and blood in both groups. Compared to the control group, the heparin-treated group had 30% less $^3$H-cholesterol/cholesterol esters per ml of blood and 50% less per gram of liver.

EXAMPLE 8

Small intestine vesicles containing approximately 50 ug of endogenous heparin were treated with 1.25 units of bacterial heparinase, the vesicles centrifuged and the amount of uronic acid residues in the supernatant and pellet quantified as a function of the length of exposure to heparinase. A time-dependent release of uronic acid fragments from the pellet into the supernatant was noted, with approximately 50% of total vesicular heparin appearing in the supernatant after four hours. Aliquots of these vesicles were then incubated with $^{125}$I-labeled cholesterol esterase to assess the binding of cholesterol esterase to these heparin-depleted vesicles. In contrast to control experiments in which cholesterol esterase was found to bind avidly to small intestine vesicles, it was observed that specific binding of $^{125}$I-cholesterol esterase to the heparin-depleted vesicles was decreased by 95%±5%. Therefore, removal of surface-bound vesicular heparin by treatment with bacterial heparinase eliminated specific binding of cholesterol esterase which in turn should eliminate absorption of free cholesterol produced at the membrane.

EXAMPLE 9

Bovine pancreatic amylase, phospholipase $A_2$, deoxyribonuclease, cholesterol esterase and triglyceride lipase were radiolabeled with $Na^{125}I$ and utilized in binding assays as described in Example 5. Blotto (1%) was utilized to block nonspecific protein binding sites and a 50-fold molar excess of unlabeled pure enzyme was added to assess nonspecific binding. As noted above for cholesterol esterase, triglyceride lipase binds to small intestine membrane vesicles and is displaced by exogenous heparin (see FIG. 4). In contrast, pancreatic enzymes (amylase, deoxyribonuclease, and phospholipase $A_2$) which hydrolyze hydrophilic substrates such as sugars do not bind to membrane-bound heparin. These results indicate that interfering with the interaction between heparin and neutral lipolytic enzymes secreted by the pancreas should markedly diminish fatty acid absorption, but have little or no effect on the metabolism of other nutrients.

EXAMPLE 10

Human pancreatic cholesterol esterase (100 kDa) and human pancreatic triglyceride lipase (52 kDa) were purified to homogeneity (Examples 1 and 3), and their abilities to cleave triglycerides and cholesteryl esters were compared. The homogeneous 52 kDa enzyme hydrolyzed triolein at a rate of 27 nmol/hr/g pancreas and this activity was inhibited by 0.15M NaCl (68%), but it was stimulated by a 10-fold excess of colipase (375%). On the other hand, the purified 100 kDa esterase protein hydrolyzed triolein at a rate of 1,970 nmol/hr/g pancreas in the presence of 5 mM taurocholate, and this activity was unaffected either by 0.15M NaCl or by a 50-fold molar excess of colipase. Since pancreatic cytosol cleaves triolein at a rate of 2,200 nmol/hr/g, these results indicate that the vast majority of triglyceride hydrolytic activity resides with the 100 kDa protein, and not with the 52 kDa species. Virtually the same results were found with cholesteryl esters; the 100 kDa enzyme cleaved cholesterol oleate at a rate at least 490-fold greater than that found for the 52 kDa triglyceride lipase. Taken together, these results suggest that in man the 100 kDa enzyme is responsible for hydrolyzing both triglycerides and cholesteryl esters.

EXAMPLE 11

The importance of heparin for the uptake of fatty acid from triolein was demonstrated in a similar way. Confluent monolayers of $2 \times 10^6$ CaCo cells (Example 5b) were incubated with 2 mM taurocholate and with [$^{14}$C]triolein (5 uM) embedded in phosphatidylcholine vesicles. In the absence of triglyceride lipase, cellular uptake of [$^{14}$C]oleate was linear and at eight hours was 204 pmol. In the presence of human triglyceride lipase (25 nM) and colipase (400 nM), uptake was brisk, reaching 706 pmol at eight hours. Moreover, enzyme-mediated uptake was also dependent on the presence of colipase in the medium, since uptake was only 229 pmol at eight hours in its absence. Heparin (400 uM) added to medium containing triglyceride lipase and colipase reduced uptake from 706 pmol to 329 pmol at eight hours. Thus, heparin decreased cellular uptake of oleate (oleic acid) from cleaved triglyceride by 75%.

EXAMPLE 12

The 500 MHz high resolution proton NMR spectra of LDL-bound heparin and bulk heparin were gathered at 24° C. in $D_2O$. Proton assignments were determined from a comparison of published values for heparin and its chemically modified derivatives (Ayotte, L. and Perlin, A. S., Carbohydrate Research 145:267–277, 1986). The spectrum for LDL-bound heparin has two differences when compared to that for bulk heparin. Thus, for LDL-bound heparin, there is a new signal at 4.85 ppm (FIG. 5), and moreover, the signal at 5.1 ppm for bulk heparin (FIG. 6) is shifted downfield to 5.3 ppm. Both these changes are consistent with the replacement of an —$OSO_3$ group in bulk heparin by an —OH group in LDL-bound heparin at the C-2 position of α-1-idopyranosyluronic acid residue.

Figure 5:
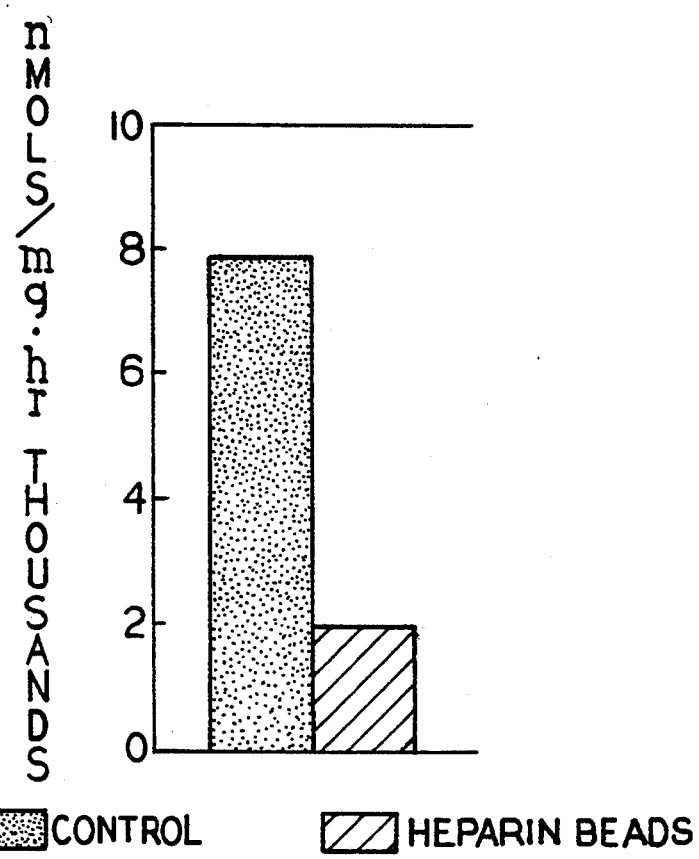
FIG. 5 is a 500 MHz high resolution proton NMR spectrum of LDL-bound heparin gathered at 24° C. in $D_2O$.
Figure 6:
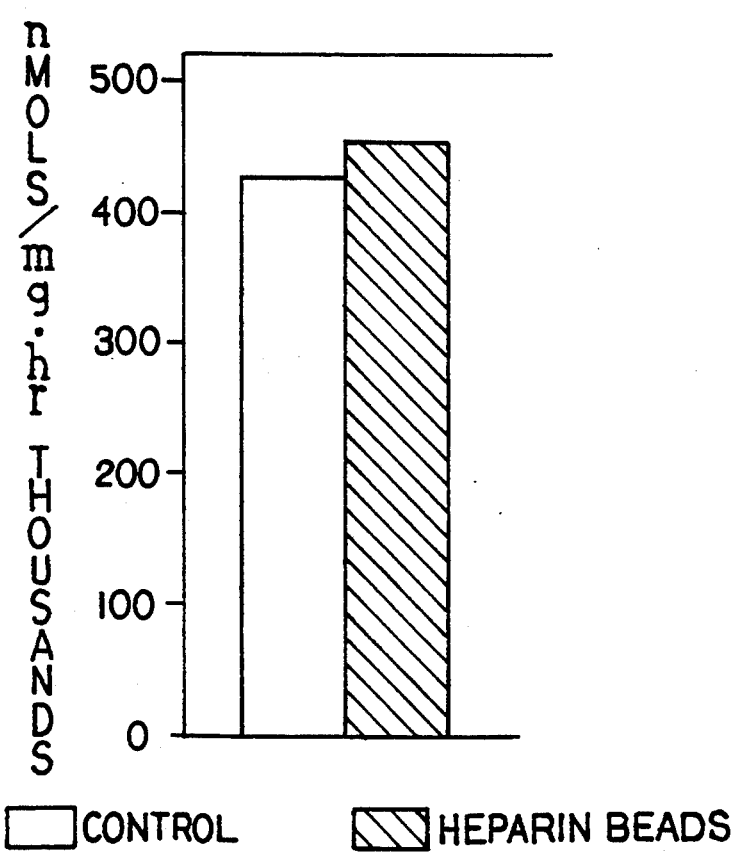
FIG. 6 is a 500 MHz high resolution proton NMR spectrum of bulk heparin gathered at 24° C. in $D_2O$.

As can be seen from a comparison of FIGS. 5 and 6, there is a clear difference between LDL-bound heparin (heparin subfraction) and bulk heparin. The heparin subfraction is characterized by greater inhibitory potency, LDL binding and a downfield proton on NMR spectra.

In view of the above, it will be seen that the several objects of the invention are achieved and other advantageous results attained.

As various changes could be made in the above methods and compositions without departing from the scope of the invention, it is intended that all matter contained in the above description shall be interpreted as illustrative and not in a limiting sense.

What is claimed is:

1. A method for preparing a solution of purified human pancreatic cholesterol esterase having a molecular weight of about 100,000 by the steps of:
   (a) preparing a dialyzed solution comprising protein impurities, and human pancreatic cholesterol esterase proteins of various molecular weights including human pancreatic cholesterol esterase having a molecular weight of about 100,000;
   (b) chromatographing the dialyzed solution of step (a) on heparin agarose;
   (c) washing the protein impurities from the heparin agarose;
   (d) eluting the human pancreatic cholesterol esterase from the heparin agarose column and collecting the band containing human cholesterol esterase having a molecular weight of about 100,000.

* * * * *